US007960877B2

(12) United States Patent
Luo

(10) Patent No.: US 7,960,877 B2
(45) Date of Patent: Jun. 14, 2011

(54) ELECTRIC RECIPROCATING MOTION DEVICE WITH SPRING MOTOR

(76) Inventor: Ming Luo, Guangdong (CN)

( * ) Notice: Subject to any disclaimer, the term of this patent is extended or adjusted under 35 U.S.C. 154(b) by 0 days.

(21) Appl. No.: 12/454,277

(22) Filed: May 14, 2009

(65) Prior Publication Data

US 2009/0243405 A1 Oct. 1, 2009

Related U.S. Application Data

(63) Continuation-in-part of application No. 12/514,796, filed as application No. PCT/CN2007/000008 on Jan. 4, 2007.

(30) Foreign Application Priority Data

Nov. 16, 2006 (CN) .......................... 2006 1 0149032

(51) Int. Cl.
*H02K 33/00* (2006.01)
*H02K 41/02* (2006.01)

(52) U.S. Cl. ........... 310/38; 310/12.22; 310/14; 310/15; 310/36; 310/37; 15/22.1

(58) Field of Classification Search .................... 310/38, 310/12.22, 14, 36, 37, 15; 15/22.1
See application file for complete search history.

(56) References Cited

U.S. PATENT DOCUMENTS 2,763,797 A * 9/1956 Dean ........................... 310/68 B
3,509,629 A * 5/1970 Fukuda et al. ................ 433/114
6,382,543 B1 * 5/2002 Chang ........................... 242/249
2004/0128781 A1 * 7/2004 Kunita et al. .................. 15/22.2
2004/0251748 A1 * 12/2004 Inagaki et al. .................. 310/14
2005/0091772 A1 * 5/2005 McKay ............................. 15/24
2006/0255665 A1 * 11/2006 Kraus et al. ...................... 310/36
2007/0011834 A1 * 1/2007 Shimizu et al. ................ 15/22.1

FOREIGN PATENT DOCUMENTS

CN 2785557 * 6/2006

OTHER PUBLICATIONS

European Office Patent web page: Abstract Translation CN2785557 (2006).*

* cited by examiner

*Primary Examiner* — Quyen Leung
*Assistant Examiner* — Jose A Gonzales Quinones
(74) *Attorney, Agent, or Firm* — Raymond Y. Chan; David and Raymond Patent Firm

(57) ABSTRACT

An electric reciprocating motion device includes a motor having a rotary shaft for outputting a reciprocating rotational power and a motion head coupling with the rotary shaft and being driven to move in a reciprocating motion along an axis of the rotary shaft and in a predetermined swing angle range. The motor is a spring motor including a motor unit and a torsion spring having two ends affixing at a motor housing and to the rotary shaft respectively. After the rotary shaft outputs a mechanical torque at one rotational direction, the torsion spring applies a spring force against the rotary shaft to drive the rotary shaft to rotate backward for generating the reciprocating rotational power. Using the spring motor in the electric reciprocating motion device, the device achieves the goals of simple mechanical structure, small volume, easy to install, and low in cost.

20 Claims, 9 Drawing Sheets

10 1 9 6 3 4

ELECTRIC RECIPROCATING MOTION DEVICE WITH SPRING MOTOR

CROSS REFERENCE OF RELATED APPLICATION

This is a Continuation-In-Part application of a non-provisional application having an application Ser. No. 12/514,796 and a filing date of May 13, 2009, which claims the foreign priority benefit of a foreign application having an application number 200610149032.3 and a filing date of Nov. 16, 2006, and a PCT international application having a PCT application number PCT/CN2007/000008 and a filing date of Jan. 4, 2007.

BACKGROUND OF THE PRESENT INVENTION

1. Field of Invention

The present invention relates to an electrical device, and more particularly to an electric reciprocating motion device with a spring motor, which is adapted for generating a reciprocating rotational output at a rotary shaft of the motor.

2. Description of Related Arts

The existing electrical devices, such as an electric toothbrush with a vertical type brush head, can be mainly cataloged into the two following types. The first one is that an eccentric wheel is coupled with an output shaft of a motor, wherein when the electric toothbrush is operated he entire toothbrush and its brush head are vibrating in a certain range of amplitude. However, the vibrating amplitude of this type of toothbrush is relatively smaller. Another type of toothbrush is applied an electromagnetic induction principle to generate an electromagnetic vibration, so as to provide the vertical reciprocating motion at the brush head. However, the structure of the second type of toothbrush is complicated, its volume is relatively larger, and the noise from the toothbrush and energy power consumption is higher.

In addition, most of the rotary shafts of conventional motors are outputting a rotatable motion in one single direction. In order to provide a reversible reciprocating motion, an external mechanical conversion device is usually applied to incorporate with the motor, or adapts a stepping motor for controlling purposes. However, it always involves complex structure, large volume, and high manufacturing cost.

SUMMARY OF THE PRESENT INVENTION

A main object of the present invention is to overcome the above drawbacks of the current techniques. The present invention provides an electric reciprocating motion device, which is convenient for use, simple in structure, small in volume, and having low noise and energy consumption.

Another object of the present invention is to provide an electric reciprocating motion device, wherein the motor, which is a spring motor, is simple in structure, small in volume, and relatively lower manufacturing cost.

Accordingly, in order to accomplish the above object, the present invention provides an electric reciprocating motion device to overcome the above drawbacks.

The electric reciprocating motion device, which comprises a reciprocating swing motor, a casing, a mounting bracket provided within the casing, a power source electrically extended from the motor, and a motion head connected to a rotary shaft of the motor.

The electric reciprocating motion device has the following advantages.

The motor is the reciprocating swing motor, wherein the motion head is driven by the reciprocating motor to reciprocatively oscillate in a predetermined angle range regarding to the rotary shaft. Accordingly, the motion heads with various formations or practical functions can be selected to detachably insert into or couple with the rotary shaft of the motor or the connection shaft thereof, the electric reciprocating motion device of the present invention can drive the motion head to provide a corresponding formation or practical function thereof.

Accordingly, in order to accomplish the above object, the present invention also can be practiced by the followings.

A motor function control circuit board is provided, wherein a control circuit of the control circuit board comprises a functional selection and speed controlling circuit, a square-wave oscillation and regulating circuit, and a motor driving circuit electrically connected in series manner.

The motion head is capable of being detachably inserted or attached to the rotary shaft, wherein the motion head provides a predetermined function at its head portion. A shape of a connection end of the motion head is flat, square, or cylindrical.

The motion head is connected to the rotary shaft of the motor via a connection shaft, wherein two opposed ends of the connecting shaft has an elongated rectangular shape with one hole formed thereat, wherein one end of the connection shaft is fixedly mounted on the rotary shaft of the motor, and the other end is detachably inserted into the connection end of motion head.

The rotary shaft of the motor further comprises a sealing ring, which is made by waterproof material.

The mounting bracket of the motor has a rectangular shaped adapted for supporting the circuit board and the power source, such as the battery, of the motor thereat.

A button is further provided on a peripheral surface of the casing and aligned with a switch of the control circuit board, so that when the button is pressed, the switch of the circuit board is controllably activated, to operatively control a working status of the motor.

The casing and a bottom cover are coupled with each other to form the hollow receiving cavity within the casing, wherein the receiving cavity receives the mounting bracket, the motor, the control circuit board, and at least one battery as the power source.

Comparing the present invention to the current techniques, the present invention has the following advantages.

The present invention is easy to use, simple in structure, small in volume, and low in noise and energy consumption. The motion head is directly driven by the motor and the connection shaft. The speed switching and other corresponding functions can be adjusted by controlling the control circuit board without changing other mechanical parts. Detaching and changing the motion head is simple and easy. Accordingly, the motion heads with various formations or practical functions can be selected to detachably insert into or couple with the rotary shaft of the motor or the connection shaft thereof, the electric reciprocating motion device of the present invention can drive the motion head to provide a corresponding formation or practical function thereof.

The present invention further provides a spring motor which comprises a motor unit, and a spring. The motor unit is a rotary shaft motor, such as a conventional DC motor, pulse motor, or AC motor, wherein the motor unit comprises a rotary shaft for outputting a rotatable motion. The motor unit could be either a brush motor or a brushless motor. The spring is a torsion spring, such as a spiral spring, having a torque function, wherein one end of the torsion spring is fixed on the rotary shaft of the motor unit, and another end of the torsion spring is fixed on a housing of the motor unit.

To compare the existing technology and the related similar products with the provided spring motor of the present invention, the spring motor has the following advantages. First, the spring motor is simple in structure. Due to the spring is directly fixed between to the rotary shaft and the housing of the motor unit, the whole structure of the spring motor is simplified and compacted. Meanwhile, the art of producing process of the spring motor is also simplified, so as to increase the production rate of the motor. To apply the spring motor to the conventional reciprocating rotation products structure, there is no need to use the complicated mechanical conversion system. Therefore, the whole device can achieve the goals of simple mechanical structure, small volume, and easy to install. When the spring motor is operating, the rotary shaft of the motor is reciprocatively rotating in a certain angle range along the axis.

These and other objectives, features, and advantages of the present invention will become apparent from the following detailed description, the accompanying drawings, and the appended claims.

DETAILED DESCRIPTION OF THE PREFERRED EMBODIMENT

Figure 1:
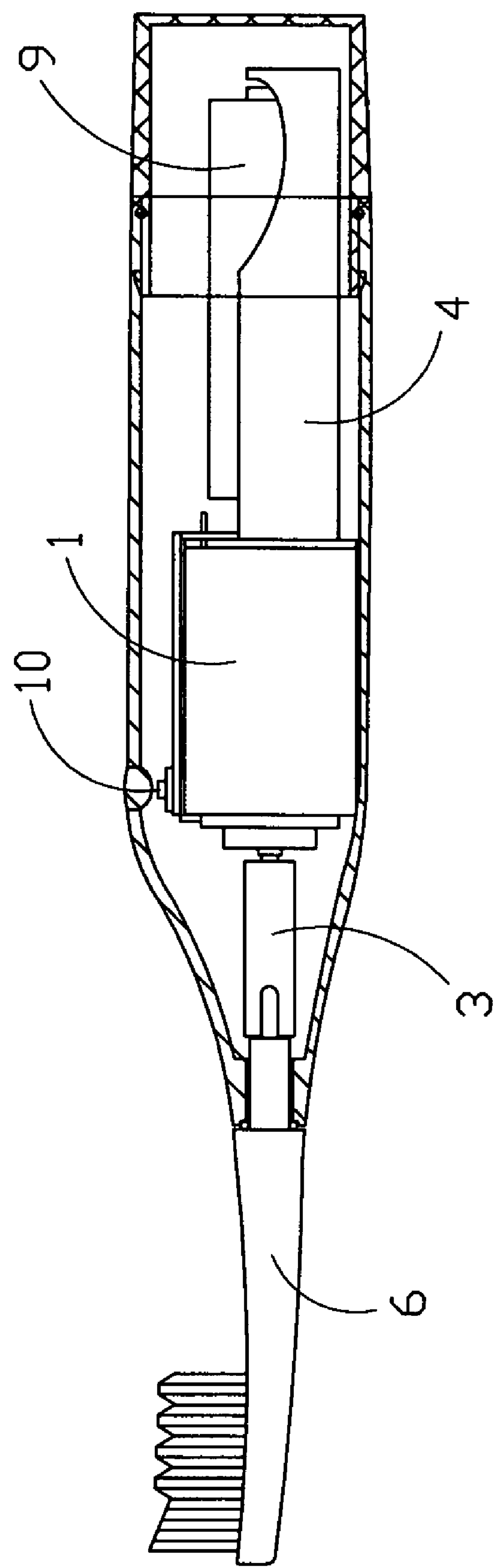
FIG. 1 is a perspective view of an electric reciprocating motion device applied for an electric toothbrush according to a preferred embodiment of the present invention.
Figure 2:
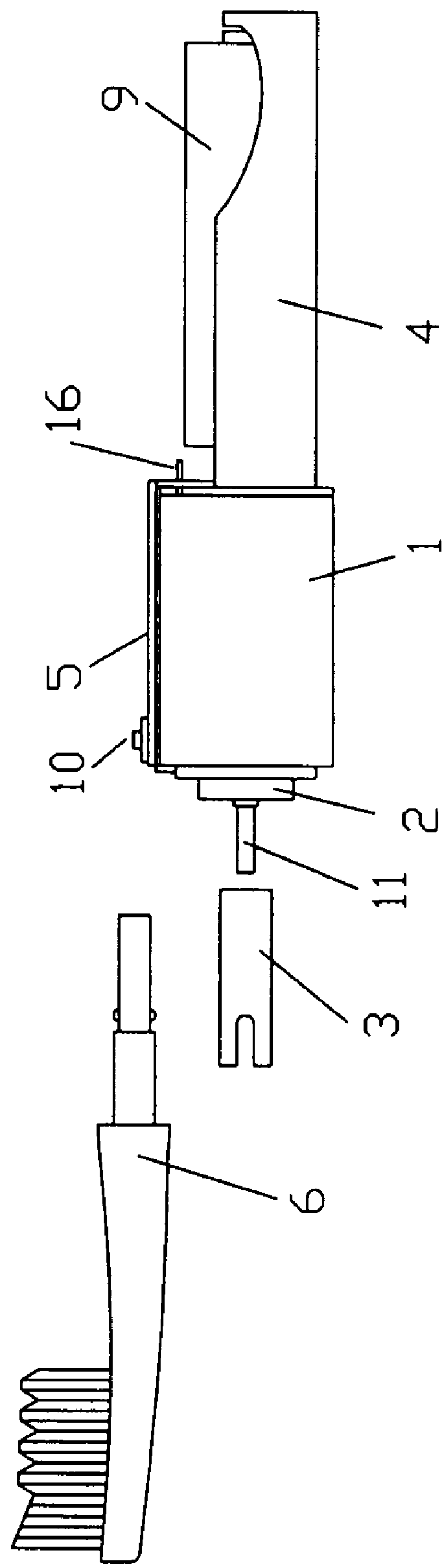
FIG. 2 is an exploded view of the electric reciprocating motion device according to the preferred embodiment of the present invention, wherein the casing and the bottom cover are omitted.
Figure 3:
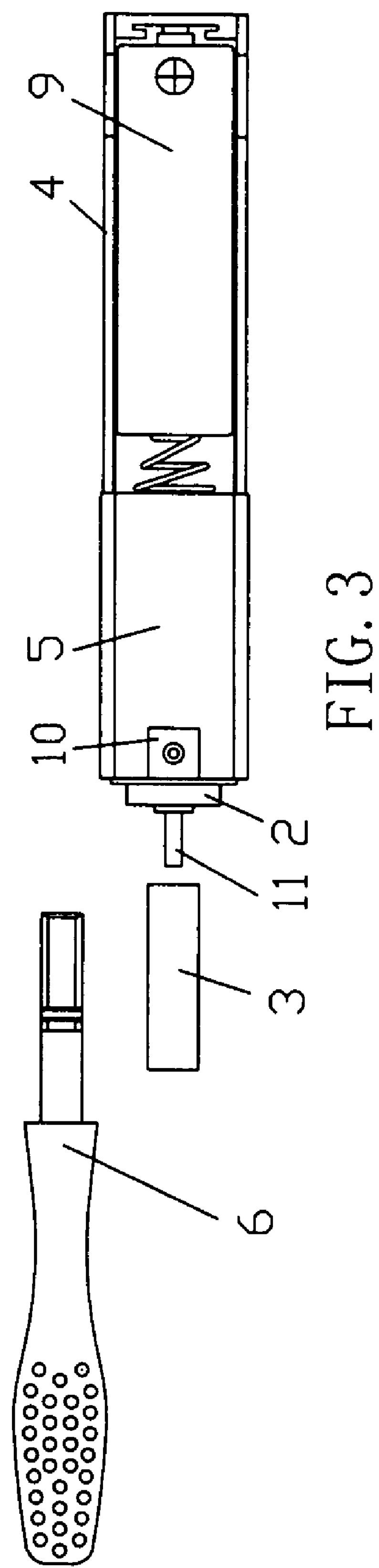
FIG. 3 is a top view of the electric reciprocating motion device according to the preferred embodiment of the present invention.
Figure 4:
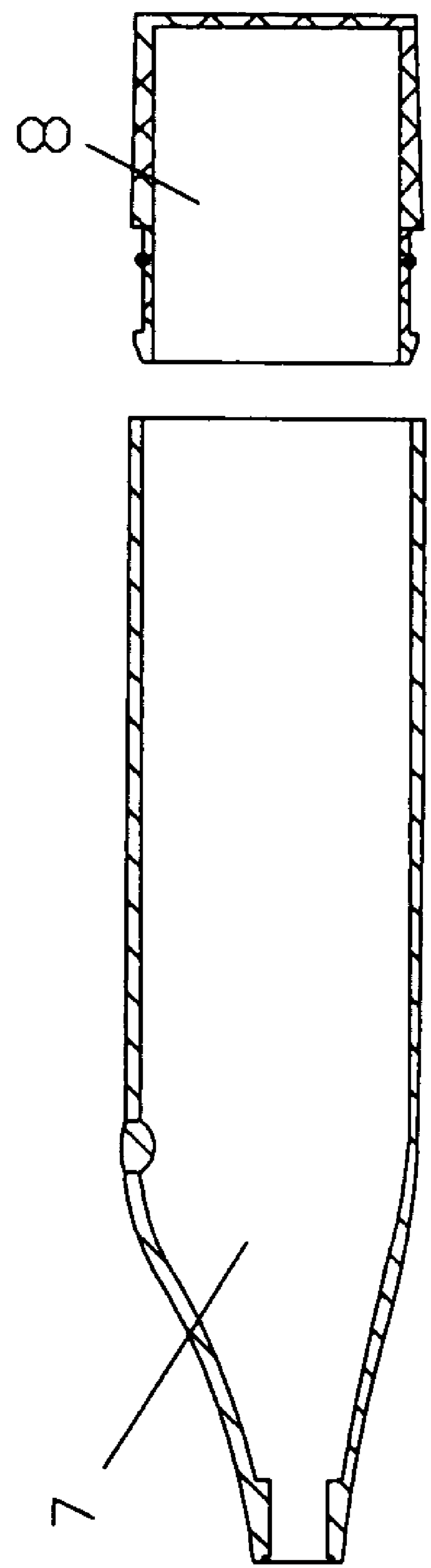
FIG. 4 is a sectional view of the casing and the bottom cover of the electric reciprocating motion device according to the preferred embodiment of the present invention.
Figure 5:
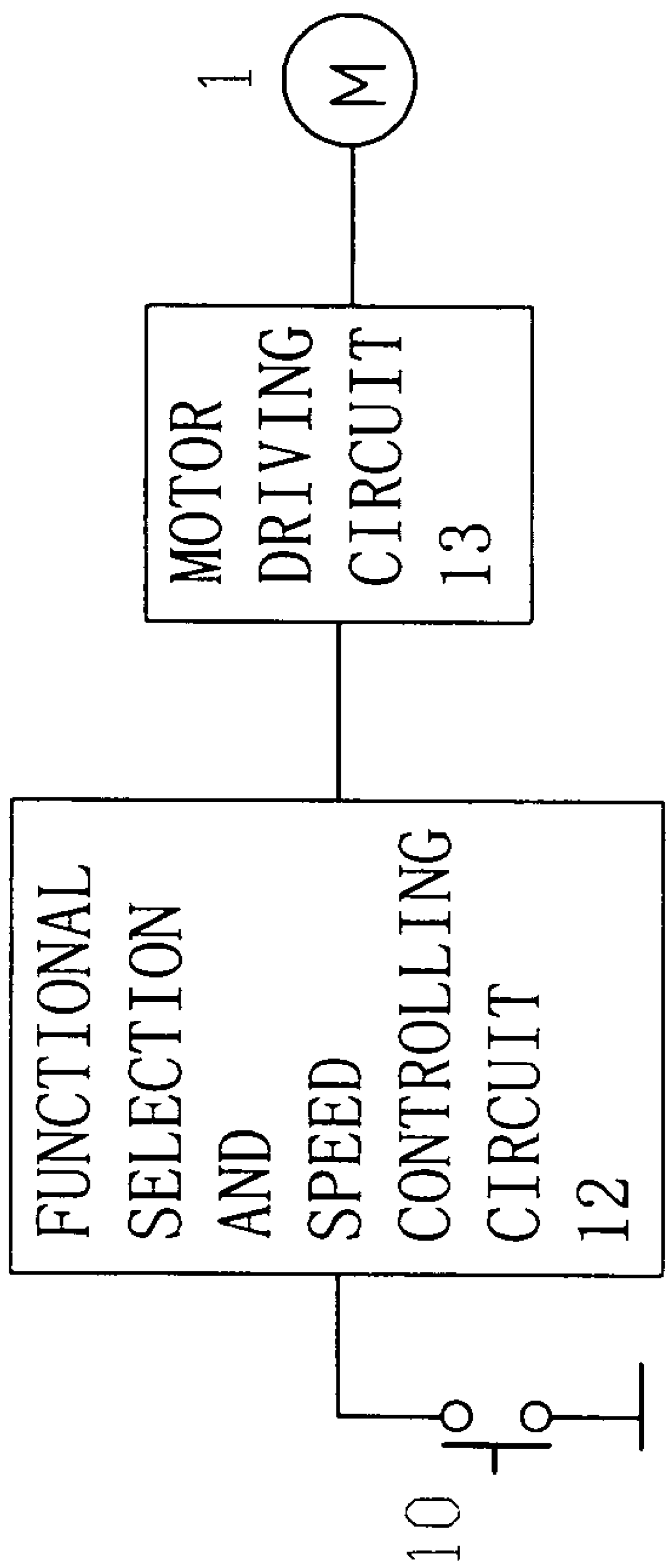
FIG. 5 is a block diagram of the control circuit board of the electric reciprocating motion device according to the preferred embodiment of the present invention.

An electric reciprocating motion device of the present invention applied on an electric toothbrush is described as followings.

Referring to FIGS. 1 to 5 of the drawings, the electric reciprocating motion device, applied to an electric vertical-type reciprocating motion toothbrush, of the present invention is illustrated. The electric toothbrush comprises a reciprocating swing motor 1, a motion head 6 as a brush head, a casing 7 and a bottom cover 8 detachably coupling thereto to form a hollow handle, a mounting bracket 4 integrally received in the hollow handle, wherein the electric reciprocating motion device is supported by the mounting bracket 4. The electric reciprocating motion device comprises a reciprocating swing motor 1, and a battery of a power source 9, and a motor control circuit board 5. The motor 1 comprises a rotary shaft 11 as an output shaft and a waterproof sealing ring 2 mounted at the motor 1 to encircle around the rotary shaft 11, wherein the motion head 6 is coupled with the rotary shaft 11 via a connection shaft 3. The electric reciprocating motion device further comprises a control switch 10 provided at an outer peripheral surface of the casing 7. The motor control circuit board 5 comprises a functional selection and speed controlling circuit 12, and a motor driving circuit 13 electrically connected in series manner to operatively control the motor 1 in a working status. When the control switch 10 is activated, the functional selection and speed controlling circuit 12, and the motor driving circuit 13 generate an outputting signal to operate the motor 1 in a working status so as to control the reciprocating speed and other corresponding functions of the rotary shaft 11 of the motor 1. Therefore, when the motion head 6 is coupled at the rotary shaft 11 of the motor 1, the motion head 6 is driven for providing a reciprocating motion thereat along an axis of the rotary shaft 11 in a predetermined angle range regarding to the rotary shaft 11, so as to drive a brush hair on the motion head 6 of the toothbrush to provide the vertically reciprocating motion to brush the teeth up and down. Thus, the up and down vertically reciprocating motion can meet the requirement of oral brushing science that dentists suggested.

The reciprocating swing motor 1 is disclosed from a prior China patent "Reciprocating swing pulse brushless motor" with the Patent number CN2498787Y which is the same applicant as the present invention. The reciprocating swing pulse brushless motor comprises a stator, a rotor, a coil unit, and a spring, wherein the stator comprises two arc-shaped permanent magnets provided at an inner side of the housing of the motor and having two different poles respectively. The magnetic poles are pointed at the center of the motor. The rotor is made of soft magnetic material and is formed as a cylindrical shaped rotor having a plurality of grooves indently formed at the outer peripheral surface of the rotor. A rotation shaft is provided at the center of the rotor. The coil unit comprises a plurality of insulated wires winding at the indented grooves and coupled with each head-to-tail in a directional manner, wherein the insulated wire has two wire ends extended outwardly in responsive to the number of coiled wire. The spring has one end fixed on a spring seat which is located at a tail end of the rotor. An opposed end of the spring is fixed on the bottom of the casing or the bottom cover. The power source 9 can be a 1.5V DC power or above, wherein the power source 9 can be a disposable battery, a rechargeable battery, or other DC regulating power source. The function selection and speed controlling circuit 12 can adapt a 74HC74 chip, 74HC14 chip, or other IC chip set.

FIGS. 6 to 12 illustrate an alternative mode of the motor of the electric reciprocating motion device, wherein the motor of the electric reciprocating motion device is a spring motor.

Figure 7:
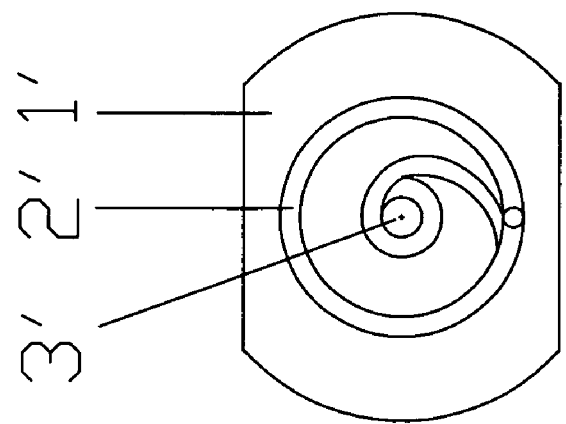
FIG. 7 is a front view of the spring motor according to the above preferred embodiment of the present invention, illustrating the torsion spring being supported at an exterior of the housing of the motor unit.
Figure 6:
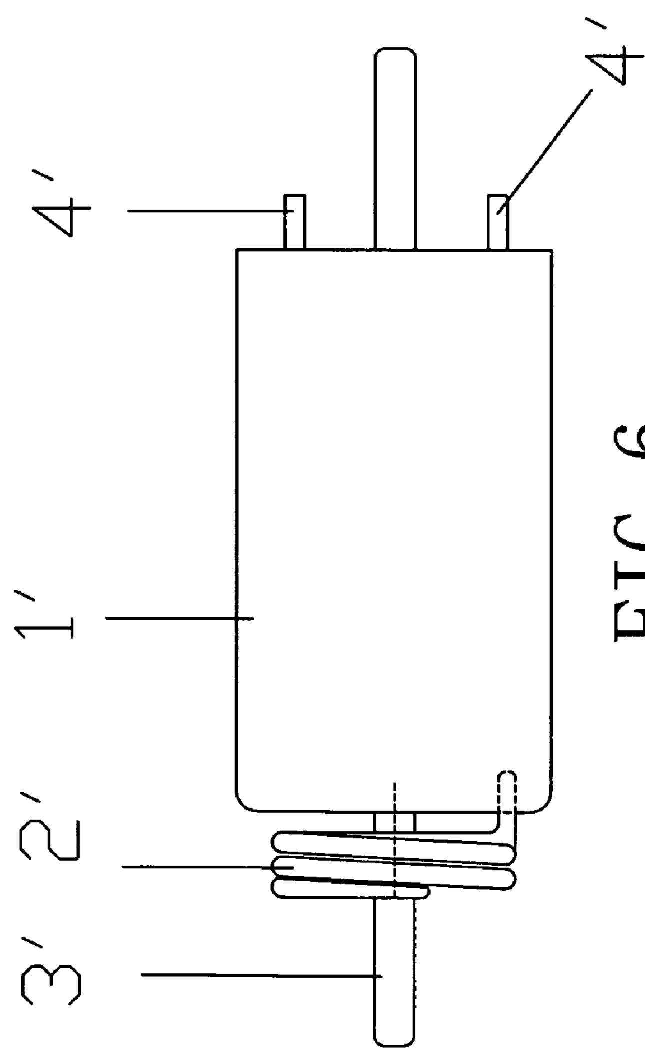
FIG. 6 is a side view of a spring motor of the electric reciprocating motion device according to the above preferred embodiment of the present invention, illustrating the torsion spring being supported at an exterior of the housing of the motor unit.
Figure 9:
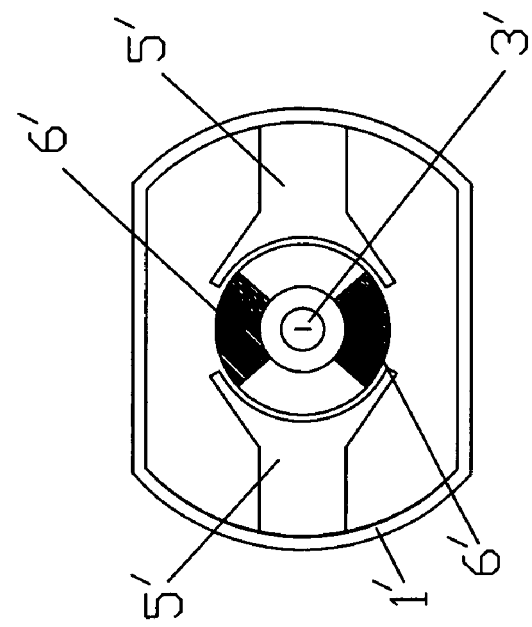
FIG. 9 is a front sectional view of the spring motor according to the above preferred embodiment of the present invention, illustrating the relationship between the stator core and the rotor permanent magnet.
Figure 8:
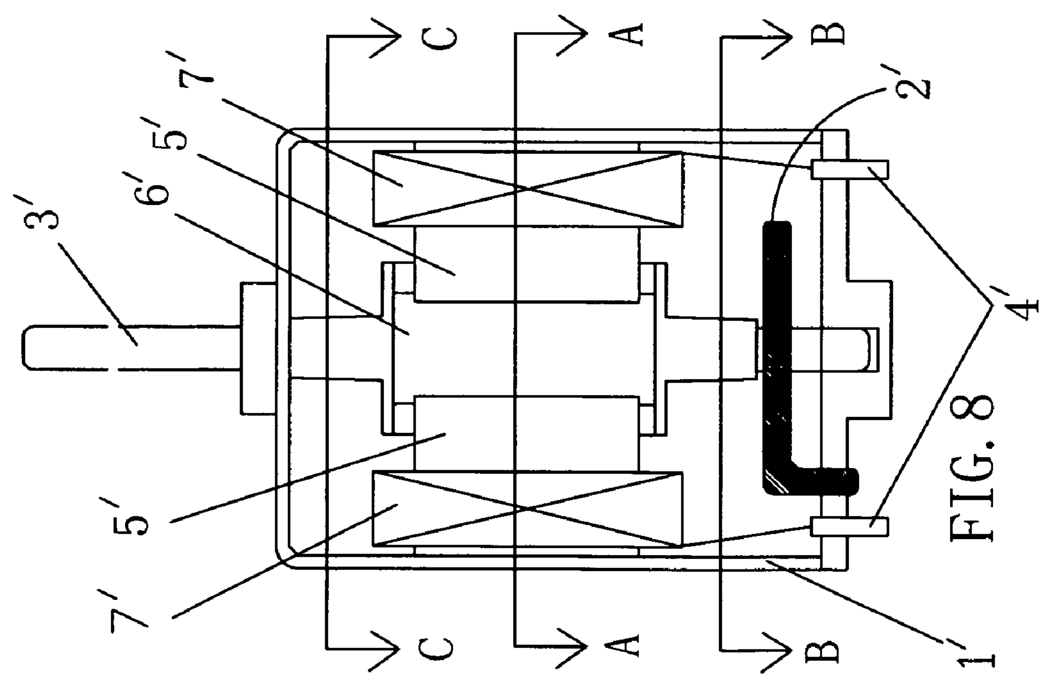
FIG. 8 is a top sectional view of the spring motor according to the above preferred embodiment of the present invention, illustrating the torsion spring being supported at an interior of the housing of the motor.
Figure 11:
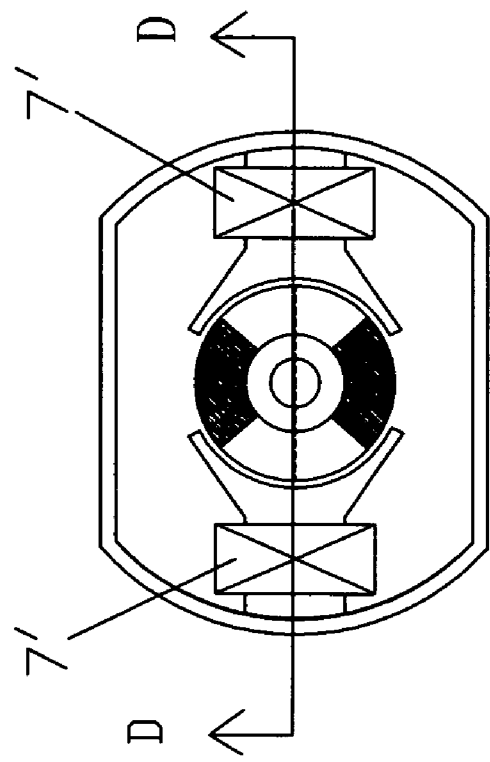
FIG. 11 is a front sectional view of the spring motor according to the above preferred embodiment of the present invention, illustrating the relationship between the stator coil-windings and the rotor permanent magnet.
Figure 10:
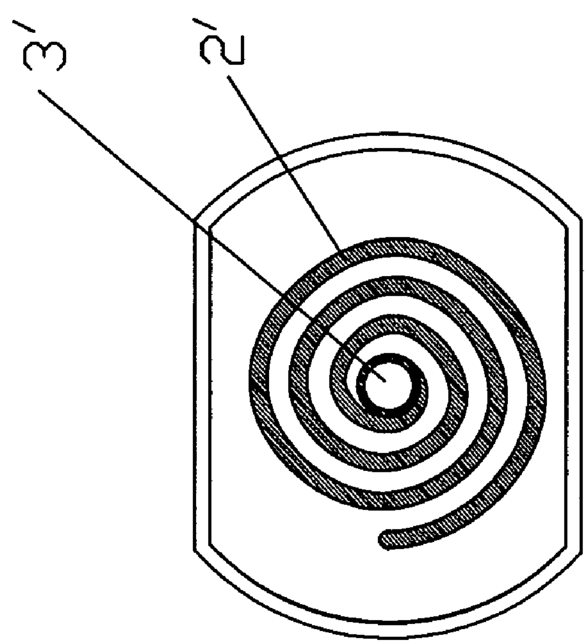
FIG. 10 is a front sectional view of the spring motor according to the above preferred embodiment of the present invention, illustrating the torsion spring being supported at an interior of the housing of the motor unit to couple with the rotary shaft.
Figure 12:
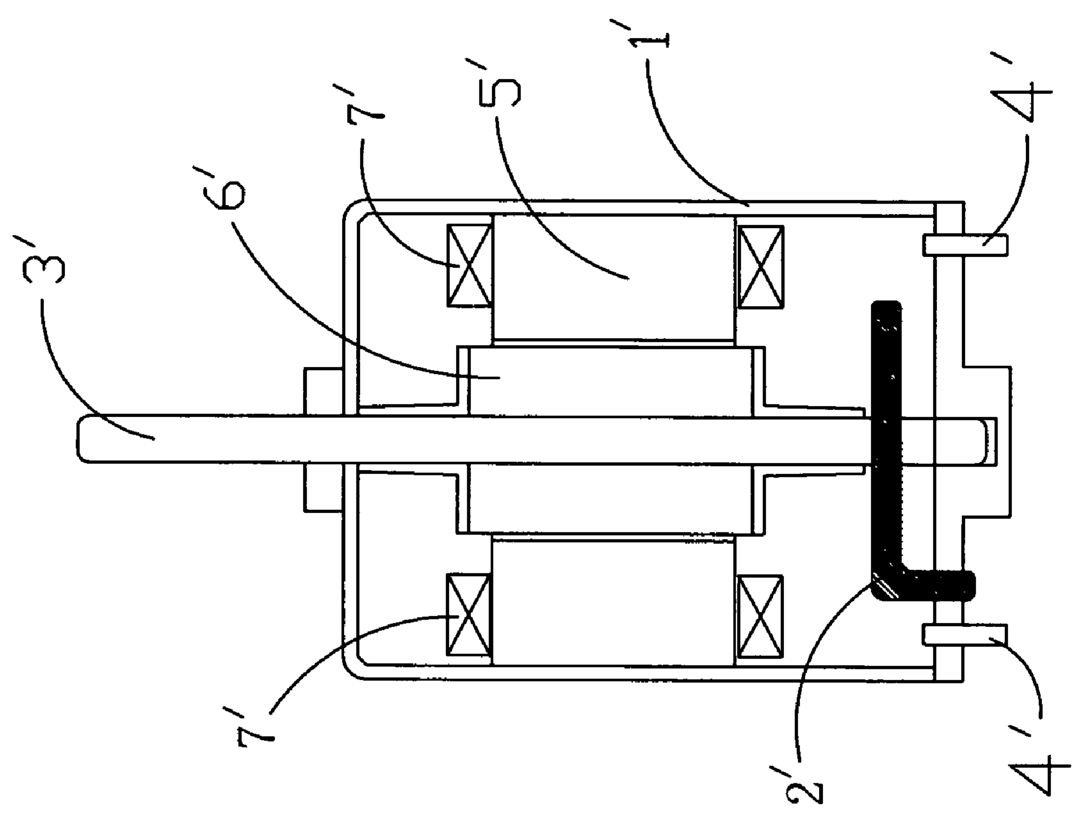
FIG. 12 a top sectional view of the spring motor according to the above preferred embodiment of the present invention, illustrating the relationship among the stator core, the stator coil-windings, and the rotor permanent magnet with respect to the torsion spring.

Referring to FIGS. 6 to 12 of the drawings, the spring motor comprises a motor housing 1', a torsion spring 2', a rotary shaft 3', a connection terminal 4', a stator core 5', a rotor permanent magnet 6', and a stator coil-windings 7' operatively received in the motor housing 1'. The torsion spring 2' has one end affixed at the rotary shaft 3' of the motor and an opposed end affixed on the motor housing 1' of the motor unit. More specifically, when one end of the torsion spring 2' is affixed at the rotary shaft 3' located at an exterior side of the motor unit, the opposed end of the torsion spring 2' is affixed at the exterior wall of the motor housing 1', as shown in FIGS. 6 and 7. In other words, the torsion spring 2' is supported at the exterior of the motor housing 1'. When one end of the torsion spring 2' is affixed at the rotary shaft 3' located at an interior side of the motor unit, the opposed end of the torsion spring 2' is then affixed at the interior wall of the motor housing 1', as shown in FIGS. 8 and 10 of the drawings. In other words, the torsion spring 2' is supported at the interior of the motor housing 1'. The relative position between the torsion spring 2' and the motor housing 1' is either affixing the torsion spring 2' at a front end of the motor housing 1' or at a rear end of the motor housing 1'. As long as the specific material, shape, and structure of the torsion spring 2' provide the torque function, it is considered that the torsion spring 2' can be utilized in the motor unit. The working principle of the spring motor is being briefly described as followings. Take a DC motor for example. When a DC pulse power source, having a constant voltage, frequency, and duty cycle, constantly inputs into the connection terminal 4' and a rotor coil-windings (or stator coil-windings 7'), the coil-windings are electrified during the high pulse period. Therefore, according to the electromagnetic induction principle, the rotary shaft 3' starts moving from a static to rotate a certain rotational angle (its direction is determined by the external power voltage). The rotary shaft 3' will output a mechanical torque at one rotational direction. The torsion spring 2' affixed at the rotary shaft 3' of the motor unit will also obtained a torque force at the same time. During the low pulse period, the coil-windings will stop electrified, so that the rotary shaft 3' is stopped rotating. The torsion spring 2' will apply a spring force against the rotary shaft 3' to drive the rotary shaft 3' to rotate backward. Therefore, the rotary shaft 3' is forced to rotate back to the static state by the spring force of the torsion spring 2', and the rotational direction of the rotary shaft 3' is opposite of the starting rotational direction. Therefore, the rotary shaft 3' of the spring motor completes a full cycle of reciprocating rotational output. When the pulse power source is continually inputting to the spring motor, the rotary shaft 3' continually keeps completing each reciprocating outputting of the mechanical torsion movement. An electric toothbrush could be one example for being incorporated and applied to the spring motor. When a toothbrush motion head is fixedly and detachably mounted to the rotary shaft 3' of the spring motor, the toothbrush motion head will have a reciprocating motion within a predetermined swing angle range while the pulse power source is inputted to the spring motor, so as to practice the effect of electric toothbrush.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An electric vertical-type reciprocating motion toothbrush, comprising:

at least a brush head;

a handle casing;

a power source received in said casing; and a spring motor supported in said casing and powered by said power source, wherein said spring motor comprises:

a motor unit;

a motor housing receiving said motor unit therein;

a rotary shaft coaxially extended from said motor unit to a front end of said motor housing to locate at an exterior side of said motor unit and said motor housing to connect with said brush head outside said handle casing; and a torsion spring which is a spiral spring being disposed around said rotary shaft and having an inner end and an outer end, wherein said inner end of said spiral spring is affixed with said rotary shaft and said outer end of said spiral spring is affixed to said motor housing, wherein a DC pulse power source, having constant voltage, frequency and duty cycle, is constantly inputted to said spring motor, said motor unit generating a pulse output to drive said rotary shaft to rotate to one rotational direction, wherein at a high pulse period, said rotary shaft starts moving from a static state to rotate a predetermined rotational angle and said rotary shaft outputs a mechanical torque at said rotational direction of said rotary shaft and said spiral spring also obtains a torque force at the same time, and at a low pulse period, said rotary shaft stops rotating and said spiral spring applies a spring force against said rotary shaft to drive said rotary shaft to rotate backward in a direction opposite to said rotational direction and be forced to rotate back to said static state by said spring force, and thus said rotary shaft of said spring motor completes a full cycle of reciprocating rotational output, wherein when said pulse power source is continually inputting to said spring motor, said rotary shaft continually keeps completing each reciprocating outputting of mechanical torsion movement and said brush head connected with said rotary shaft is driven to provide a vertically reciprocating motion for brushing teeth up and down within a predetermined swing angle range while said pulse power source is inputted to said spring motor.

2. The electric vertical-type reciprocating motion toothbrush, as recited in claim 1, wherein said spiral spring is disposed at said exterior side of said motor housing, wherein said outer end of said spiral spring is affixed to an exterior wall of said motor housing and said inner end of said spiral spring is spirally extended around said rotary shaft and affixed to said rotary shaft located at said exterior side of said motor housing.

3. The electric vertical-type reciprocating motion toothbrush, as recited in claim 1, wherein said rotary shaft has another end extended from the other end of said motor unit to a rear end of said motor housing, wherein said spiral spring is in planar form and disposed in said motor housing and said outer end of said spiral spring is affixed to an interior wall of said motor housing while said inner end of said spiral spring is spirally extended around and affixed to said another end of said rotary shaft located at an interior side of said motor housing.

4. The electric vertical-type reciprocating motion toothbrush, as recited in claim 1, wherein said spring motor further comprises a connection terminal, and said motor unit comprises a stator core, a rotor permanent magnet, and a stator coil-windings received in said motor housing, wherein when said pulse power source is constantly inputted into said connection terminal and said stator coil-windings, said stator coil-windings are electrified during said high pulse period to electromagnetically induct with said magnet so as to drive said rotary shaft for outputting said mechanical torque at said rotational direction, so that said rotary shaft starts moving from said static to rotate said predetermined rotational angle.

5. The electric vertical-type reciprocating motion toothbrush, as recited in claim 2, wherein said spring motor further comprises a connection terminal, and said motor unit comprises a stator core, a rotor permanent magnet, and a stator coil-windings received in said motor housing, wherein when said pulse power source is constantly inputted into said connection terminal and said stator coil-windings, said stator coil-windings are electrified during said high pulse period to electromagnetically induct with said magnet so as to drive said rotary shaft for outputting said mechanical torque at said rotational direction, so that said rotary shaft starts moving from said static to rotate said predetermined rotational angle.

6. The electric vertical-type reciprocating motion toothbrush, as recited in claim 3, wherein said spring motor further comprises a connection terminal, and said motor unit comprises a stator core, a rotor permanent magnet, and a stator coil-windings received in said motor housing, wherein when said pulse power source is constantly inputted into said connection terminal and said stator coil-windings, said stator coil-windings are electrified during said high pulse period to electromagnetically induct with said magnet so as to drive said rotary shaft for outputting said mechanical torque at said rotational direction, so that said rotary shaft starts moving from said static to rotate said predetermined rotational angle.

7. The electric vertical-type reciprocating motion toothbrush, as recited in claim 1, further comprising a motor control circuit board electrically connected to said motor for controlling an operation of said motor, wherein said motor control circuit board comprises a function selection and speed controlling circuit and a motor driving circuit electrically connected in a series manner to control said motor.

8. The electric vertical-type reciprocating motion toothbrush, as recited in claim 4, further comprising a motor control circuit board electrically connected to said motor for controlling an operation of said motor, wherein said motor control circuit board comprises a function selection and speed controlling circuit and a motor driving circuit electrically connected in a series manner to control said motor.

9. The electric vertical-type reciprocating motion toothbrush, as recited in claim 5, further comprising a motor control circuit board electrically connected to said motor for controlling an operation of said motor, wherein said motor control circuit board comprises a function selection and speed controlling circuit and a motor driving circuit electrically connected in a series manner to control said motor.

10. The electric vertical-type reciprocating motion toothbrush, as recited in claim 6, further comprising a motor control circuit board electrically connected to said motor for controlling an operation of said motor, wherein said motor control circuit board comprises a function selection and speed controlling circuit and a motor driving circuit electrically connected in a series manner to control said motor.

11. The electric vertical-type reciprocating motion toothbrush, as recited in claim 1, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

12. The electric vertical-type reciprocating motion toothbrush, as recited in claim 2, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

13. The electric vertical-type reciprocating motion toothbrush, as recited in claim 3, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

14. The electric vertical-type reciprocating motion toothbrush, as recited in claim 4, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

15. The electric vertical-type reciprocating motion toothbrush, as recited in claim 5, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

16. The electric vertical-type reciprocating motion toothbrush, as recited in claim 6, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

17. The electric vertical-type reciprocating motion toothbrush, as recited in claim 7, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

18. The electric vertical-type reciprocating motion toothbrush, as recited in claim 8, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

19. The electric vertical-type reciprocating motion toothbrush, as recited in claim 9, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

20. The electric vertical-type reciprocating motion toothbrush, as recited in claim 10, further comprising a connection shaft for connecting said rotary shaft with said brush head, wherein two ends of said connection shaft are formed in an elongated rectangular shape with two holes provided thereat respectively, wherein one end of said connection shaft is coupled with said rotary shaft while another end of said connection shaft is coupled with said brush head.

* * * * *